United States Patent [19]

Carenzi et al.

[11] Patent Number: 4,960,788
[45] Date of Patent: Oct. 2, 1990

[54] PYRROLIDONE-2 COMPOUNDS AND THEIR USE FOR CENTRAL ANALGESIC ACTIVITY

[75] Inventors: Angelo Carenzi, Busto Arsizio; Dario Chiarino, Monza; Davide Della Bella, Milan; Gian Carlo Grancini, Nova Milanese; Carlo Veneziani, Bresso, all of Italy

[73] Assignee: Zambon Group S.p.A., Vicenza, Italy

[21] Appl. No.: 354,361

[22] Filed: May 19, 1989

[30] Foreign Application Priority Data

May 20, 1988 [IT] Italy .................................. 20648 A/88
Feb. 17, 1989 [IT] Italy .................................. 19480 A/89

[51] Int. Cl.$^5$ .................. C07D 207/273; A61K 31/40
[52] U.S. Cl. ..................................... 514/424; 548/550; 546/268; 546/275; 546/281; 546/261; 546/208
[58] Field of Search .......................... 548/580; 514/424

[56] References Cited

U.S. PATENT DOCUMENTS

| | | | |
|---|---|---|---|
| 2,496,163 | 1/1949 | Jacobsen | 548/550 |
| 4,320,137 | 3/1982 | Paioni | 514/424 |
| 4,525,476 | 6/1985 | Batler et al. | 548/550 |
| 4,670,456 | 6/1987 | Weber et al. | 548/550 |
| 4,767,759 | 8/1988 | Weber et al. | 548/550 |
| 4,833,140 | 5/1989 | Weber et al. | 548/550 |

FOREIGN PATENT DOCUMENTS 2549053 1/1985 France .................................. 514/424
1405148 9/1975 United Kingdom .

Primary Examiner—David B. Springer
Attorney, Agent, or Firm—Stevens, Davis, Miller & Mosher

[57] ABSTRACT

Compounds of formula

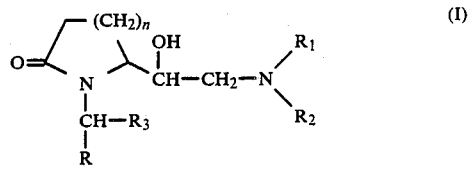

(wherein R, $R_1$, $R_2$, $R_3$ and n have the meanings reported in the specification), their salts with pharmaceutically acceptable acids, process for their preparation and pharmaceutical compositions containing them are described.

The compounds of formula I have a remarkable analgesic activity.

8 Claims, No Drawings

PYRROLIDONE-2 COMPOUNDS AND THEIR USE FOR CENTRAL ANALGESIC ACTIVITY

The present invention relates to derivatives of 2-aminoethanol and, more particularly, it relates to compounds of formula

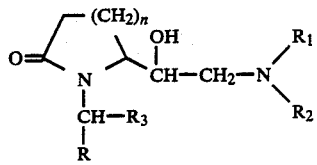

wherein

R is a phenyl optionally substituted by from 1 to 3 substituents selected among $C_1$-$C_4$ alkyl, $C_1$-$C_4$ alkoxy, hydroxy, halogen and trifluoromethyl or a 5- or 6-membered heteroaryl, containing from 1 to 3 heteroatoms selected among nitrogen, oxygen and sulfur, optionally substituted by from 1 to 3 substituents selected among $C_1$-$C_4$ alkyl, $C_1$-$C_4$ alkoxy, hydroxy, halogen;

$R_1$ and $R_2$, the same or different, are a linear or branched $C_1$-$C_6$ alkyl, a $C_3$-$C_6$ cycloalkyl; or $R_1$ and $R_2$, together with the nitrogen atom to which they are bonded, are a 5- or 6-membered heterocycle, which may further contain 1 or 2 heteroatoms selected among nitrogen oxygen and sulfur, optionally substituted by 1 or 2 $C_1$-$C_4$ alkyl groups;

$R_3$ is a hydrogen atom or a phenyl optionally substituted by from 1 to 3 substituents selected among $C_1$-$C_4$ alkyl, $C_1$-$C_4$ alkoxy, hydroxy, halogen and trifluoromethyl;

n is an integer selected between 1 and 2.

By the term linear or branched $C_1$-$C_6$ alkyl we refer to methyl, ethyl, propyl, isopropyl, butyl, isobutyl, sec.-butyl, t.butyl, n.pentyl, 3-pentyl, isopentyl, neopentyl, hexyl and isohexyl groups.

By the term $C_3$-$C_6$ cycloalkyl we refer to cyclopropyl, cyclobutyl, cyclopentyl and cyclohexyl groups.

Specific examples of heterocycle are pyrrolidine, piperidine, morpholine, piperazine, N-methylpiperazine and 2,6-dimethylpiperidine.

Specific examples of heteroaryl are isoxazole, pyridine and thiophene.

The compounds of formula I have at least two asymmetric centers and they can be in the form of stereoisomeric mixtures or of a single stereoisomer obtainable by stereoselective synthesis or by separation from the stereoisomeric mixture.

Therefore the stereoisomeric mixtures as well as the single stereoisomers of the compounds of formula I are an object of the present invention.

A further object of the invention are the salts of the compounds of formula I with organic or inorganic acids suitable for pharmaceutical use.

Examples of suitable acids are hydrochloric, hydrobromic, sulfuric, citric, succinic, p.hydroxybenzoic, maleic, glycolic acid. Preferred compounds of formula I are the compounds wherein R is a phenyl or an isoxazole, optionally substituted by from 1 to 3 substituents selected among chlorine and bromine atoms, methyl, ethyl, methoxy, ethoxy, hydroxy and trifloromethyl groups; n is 1; $R_1$ and $R_2$ are both a sec.butyl group; $R_3$ is a hydrogen atom.

A more preferred embodiment of the present invention is represented by the compounds of formula I wherein $R_1$ and $R_2$ are both a (R)-sec.butyl group.

The compounds of formula I have a remarkable central analgesic activity and they can be used in pharmaceutical field in balanced anaesthesia and in the treatment of dolorous syndromes from different origin, such as for example neoplastic origin or consequent upon a surgical operation.

The preparation of the compounds of formula I object of the present invention is carried out according to the following reaction scheme.

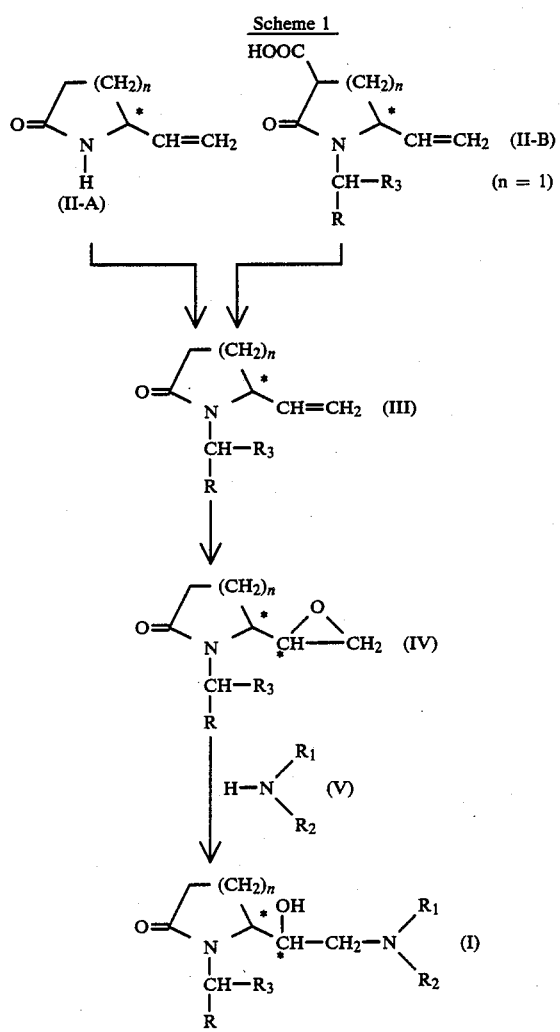

(wherein R, $R_1$, $R_2$, $R_3$ and n have the above reported meanings and the asterisks show the asymmetric carbon atoms).

The vinyl-pyrrolidinone or piperidinone of formula II-A is transformed into the corresponding N-substituted derivative of formula III.

Alternatively, the intermediate III wherein n=1 can be prepared also by decarboxylation of the carboxyderivative of formula II-B. Subsequently the intermediate III is oxidized in order to obtain the epoxide of formula IV.

From the epoxide IV the compound of formula I is prepared by reaction with a suitable amine of formula

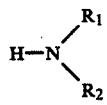

wherein $R_1$ and $R_2$ have the above reported meanings.

The compounds of formula II-A and II-B are known or easily obtainable by known methods.

In particular, the compounds of formula II-A are described in European Patent Application No. 144664 (Gruppo Lepetit S.p.A.), while the compounds of formula II-B are easily obtainable from known compounds according to the method described in Belgian Patent No. 873766 (Merrel Toraude et Compagnie).

A practical embodiment of the present invention is the following. 5-ethenyl-2-pyrrolidinone (II-A; n=1) or 6-ethenyl-2-piperidinone (II-A; n=2) are reacted with a suitable halide of formula

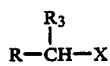

wherein R and $R_3$ have the above reported meanings and X represents a halogen atom, preferably chlorine or bromine.

The reaction is carried out in the presence of alkali metals, such as for example sodium and potassium, of alkali metal hydrides, such as for example sodium hydride or potassium hydride or other alkali metal derivatives such as for example sodium amide and potassium amide in an inert organic solvent such as dioxane, xylene, toluene, dimethylformamide, dimethylsulfoxide, tetrahydrofuran at a temperature between 0° C. and 50° C.

Alternatively, in the preparation of the compounds of formula III wherein $R_3$ is different from hydrogen, the starting compound II-A is reacted with an alcohol of formula

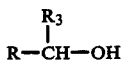

wherein R and $R_3$ have the above reported meanings, in acetic acid and in the presence of p.toluenesulfonic acid.

The intermediate of formula III is then oxidized in order to obtain the corresponding epoxide of formula IV.

The epoxidation reaction is carried out directly on the intermediate III by using peracids, oxygen or peroxides as oxidizing agents.

Examples of suitable peracids are m.chloroperbenzoic acid, peracetic acid, perbenzoic acid, trifluoroperacetic acid, 3,5-dinitroperoxybenzoic acid.

Examples of suitable peroxides are hydrogen peroxide, t.butyl peroxide and titanium tetraisopropoxide.

Exclusively for practical and economical reasons, m.chloroperbenzoic acid in an organic solvent such as chloroform, dichloromethane, dichloroethane is preferably used.

Alternatively, especially in the presence of easily oxidable groups in the intermediate of formula III, the epoxide IV, may be prepared as follows. The intermediate III is oxidized first to the corresponding diol derivative by using, for example, osmium tetroxide or potassium permanganate, and then the diol derivative is transformed into the epoxide IV by treatment with a base.

The epoxide IV gives the compounds of formula I object of the present invention by reaction with a suitable amine of formula V. Examples of suitable amines of formula V are dimethylamine, methylethylamine, diethylamine, di-n.propylamine, di-isopropylamine, dibutylamine, di-isobutylamine, di-sec.butylamine, (R,R)-di-sec.butylamine, (S,S)-di-sec.butylamine, (R,S)-di-sec.-butylamine, piperidine, pyrrolidine, piperazine, N-methyl-piperazine, morpholine, 2,6-dimethyl-piperidine, dicyclopropylamine, dicyclobutylamine, dicyclopentylamine, dicyclohexylamine, di-(3-pentyl)amine, N-(2-butyl)-N-isopropylamine.

The amine of formula V is generally used in excess and it may also act as a solvent.

Optionally the reaction may be carried out by using organic solvents such as aliphatic alcohols, aliphatic and aromatic hydrocarbons, or ethers.

An alternative method for the preparation of the compounds of formula I wherein n=1 consists in using 3-carboxy-5-ethenyl-2-pyrrolidinones of formula II-B as starting compounds.

These compounds, which can be prepared from esters of 2-ethenylcyclopropane-1,1-dicarboxylic acid according to the method described in Belgian Patent No. 873766, are directly decarboxylated, without isolation, by heating, giving the 5-ethenyl-2-pyrrolidinones of formula III.

By oxidation and condensation with an amine V according to what above reported, the compounds of formula I wherein n=1 are obtained.

The compounds of formula I have at least two asymmetric centers, which have been marked by asterisks in Scheme 1, and therefore they can be in the form of single stereoisomers or in the form of stereoisomeric mixtures.

Further asymmetric centers may be optionally present on substituents R, $R_1$, $R_2$ and $R_3$.

If the compounds of formula I are obtained as a stereoisomeric mixture, the single stereoisomers can be separated by conventional techniques such as crystallization and chromatography.

Analogously, the separation can be carried out on one of the intermediates of the synthesis and particularly on the epoxide of formula IV.

It is clear to the man skilled in the art that, by the process reported in Scheme 1, the compounds of formula I can be obtained stereoselectively.

For example, starting from a compound of formula II-A or II-B with predetermined configuration, an epoxide of formula IV as a single stereoisomer may be obtained by a stereoselective epoxidation. Then, the reaction of the epoxide IV, obtained by stereoselective synthesis or by separation from stereoisomeric mixture, with an amine of formula V gives the stereoisomerically pure compounds of formula I.

When further asymmetric centers are present on substituents $R_1$ and $R_2$, the stereoisomerically pure compounds of formula I are obtained by using amines of formula V with predetermined configuration such as (R,R)-di-sec.butylamine, (S,S)-di-sec.butylamine, (R,S)-di-sec.butylamine and N-[2(R)-butyl]-N-isopropylamine.

Preferred compounds are those in which the carbon atoms marked by an asterisk in the formula I reported in Scheme 1 have both S configuration.

The salts of the compounds of formula I with pharmaceutically acceptable acids are prepared according to conventional techniques. The pharmacological evaluation of the compounds object of the present invention proved that they have a high affinity and a remarkable activity towards opioid receptors and that they have remarkable antinociceptive properties making them particularly suitable for the use in therapy as central analgesics which are more active and have less side effects than morphine and related compounds, because they do not induce physical dependence.

In particular the pharmacological activity has been showed, in comparison with morphine, by in vitro tests, such as the evaluation of the competition for binding of [$^3$H]-dihydromorphine (DHM) to opioid receptors and the evaluation of the morphine-like activity on guineapig isolated ileum (described in example 12), as well as by in vivo tests such as hot-plate test on mouse (described in example 13) and jumping test (described in example 14).

Toxicity tests were carried on mice by subcutaneous administration of increasing doses of the compounds of formula I in order to evaluate the acute toxicity, expressed as $LD_{50}$.

The compounds of formula I showed $LD_{50}$ values higher than 300 mg/kg s.c. with a quite favourable therapeutic index between 100 and 10,000.

The compounds object of the present invention can be administered at therapeutical doses between 1 and 500 mg/day by oral route and between 1 and 500 μg/day by intravenous or intramuscular route. The pharmaceutical compositions containing the compounds of formula I or pharmaceutically acceptable salts thereof as active ingredient are a further object of the present invention.

Such compositions may contain the active ingredient together with suitable solid or liquid pharmaceutical excipients and they can be administered by oral or parenteral route.

The pharmaceutical compositions, obtainable according to known methods, can be solid such as tablets, coated tablets, capsules, powders, freeze-dried powders to be diluted at the moment of use and granulates, or liquid such as solutions, suspensions, emulsions.

In addition they can contain further usual excipients such as preserving agents, stabilizing agents, wetting agents, emulsifying agents, salts to regulate the osmotic pressure, buffers, colouring agents, flavouring agents.

In order to better illustrate the present invention the following examples are now given.

EXAMPLE 1

Preparation of (5S)-1-[(2-chlorophenyl)methyl]-5-ethenyl-2-pyrrolidinone

80% NaH in oil (3.57 g; 0.1188 moles) was added in portions to a solution of (5S)-5-ethenyl-2-pyrrolidinone (12 g; 0.108 moles) in dimethylformamide (120 ml), keeping the temperature at about 20° C. After about 30 minutes, NaI (0.8 g; 0.0054 moles) was added and then, at room temperature, 2-chlorobenzyl chloride (19.13 g; 0.1188 moles) was added dropwise.

The reaction mixture was kept under stirring at room temperature for 3 hours and then poured into a mixture of water and ice (320 ml).

After extraction with ethyl ether, the collected organic phases were washed with water and dried on sodium sulfate.

After evaporation of the solvent, an oil was obtained and distilled at 125°–130° C./0.3 mmHg giving (5S)-1-[(2-chlorophenyl)methyl]-5-ethenyl-2-pyrrolidinone (24.4 g; 96% yield).
$[\alpha]_D^{20} = +131.7°$ (c=2.4%, ethanol).
$^1$H-NMR (200 MHz, CDCl$_3$-TMS): delta (ppm): 1.71–1.87 (m, 1H); 2.13–2.61 (m, 3H); 3.92 (m, 1H); 4.54 (AMq, 2H, delta$_A$=4.88, delta$_M$=4.20, $J_{AM}$=15.6 Hz); 5.06–5.19 (m, 2H); 5.55–5.73 (m, 1H); 7.15–7.35 (m, 4H).

By working in a similar way the following compounds were prepared.

(5R)-1-[(2-chlorophenyl)methyl]-5-ethenyl-2-pyrrolidinone b.p.=145°–150° C./0.6 mmHg-92% yield.
$[\alpha]_D^{20} = -128.8°$ (c=2%, ethanol).
$^1$H-NMR (200 MHz, CDCl$_3$-TMS): delta (ppm): 1.71–1.87 (m, 1H); 2.13–2.61 (m, 3H); 3.92 (m, 1H); 4.54 (AMq, 2H, delta$_A$=4.88, delta$_M$=4.20, $J_{AM}$=15.6 Hz); 5.06–5.19 (m, 2H); 5.55–5.73 (m, 1H); 7.15–7.35 (m, 4H).

(5S)-5-ethenyl-1-(phenylmethyl)-2-pyrrolidinone b.p.=115°–118° C./0.4 mmHg-85% yield.
$[\alpha]_D^{20} = +176.2°$ (c=2%, 95% ethanol).
$^1$H-NMR (200 MHz, CDCl$_3$-TMS): delta (ppm): 1.66–1.83 (m, 1H); 2.07–2.58 (m, 3H); 3.87 (m, 1H); 4.41 (AMq, 2H, delta$_A$=4.98, delta$_M$=3.84, $J_{AM}$=14.9 Hz); 5.08–5.24 (m, 2H); 5.55–5.73 (m, 1H); 7.18–7.35 (m, 5H).

(5S)-5-ethenyl-1-[(2-fluorophenyl)methyl]-2-pyrrolidinone b.p.=109°–112° C./0.3 mmHg-93% yield.
$[\alpha]_D^{20} = +131.5°$ (c=2.4%, ethanol).
$^1$H-NMR (200 MHz, CDCl$_3$-TMS): delta (ppm): 1.68–1.85 (m, 1H); 2.10–2.58 (m, 3H); 3.91 (m, 1H); 4.47 (AMq, 2H, delta$_A$=4.83, delta$_M$=4.10, $J_{AM}$=15.2 Hz); 5.10–5.72 (m, 1H); 6.95–7.31 (m, 4H).

(5S)-5-ethenyl-1-[(3-methoxyphenyl)methyl]-2-pyrrolidinone b.p.=140°–142° C./0.3 mmHg-94% yield.
$[\alpha]_D^{20} = +156.8°$ (c=2%, ethanol).
$^1$H-NMR (200 MHz, CDCl$_3$-TMS): delta (ppm): 1.64–1.81 (m, 1H); 2.05–2.56 (m, 3H); 3.75 (s, 3H); 3.86 (m, 1H); 4.36 (AMq, 2H, delta$_A$=4.93, delta$_M$=3.79, $J_{AM}$=14.7 Hz); 5.08–5.22 (m, 2H); 5.53–5.71 (m, 1H); 6.73–6.79 (m, 3H); 7.15–7.23 (m, 1H).

(5S)-1-[(3,4-dichlorophenyl)methyl]-5-ethenyl-2-pyrrolidinone m.p.=57°–58° C. (n.hexane)-93% yield.
$[\alpha]_D^{20} = +128.0°$ (c=2%, ethanol).
$^1$H-NMR (200 MHz, CDCl$_3$-TMS): delta (ppm): 1.67–1.85 (m, 1H); 2.10–2.58 (m, 3H); 3.86 (m, 1H); 4.34 (AMq, 2H, delta$_A$=4.82, delta$_M$=3.86, $J_{AM}$=14.9 Hz); 5.10–5.25 (m, 2H); 5.51–5.69 (m, 1H); 7.05 (dd, 1H); 7.29 (d, 1H); 7.36 (d, 1H).

(5S)-1-[(4-bromophenyl)methyl]-5-ethenyl-2-pyrrolidinone b.p.=1.38°–140° C./0.4 mmHg-95% yield.
$[\alpha]_D^{20} = +116.2°$ (c=2%, ethanol).
$^1$H-NMR (200 MHz, CDCl$_3$-TMS): delta (ppm): 1.64–1.82 (m, 1H); 2.06–2.56 (m, 3H); 3.80–3.88 (m, 1H); 4.32 (ABq, 2H, delta$_A$=4.84, delta$_B$=3.81, $J_{AB}$=14.5

Hz); 5.07–5.21 (m, 2H); 5.50–5.70 (m, 1H); 7.05–7.41 (m, 4H).

(5S)-5-ethenyl-1-[(3-trifluoromethylphenyl)methyl]-2-pyrrolidinone b.p.=103°–105° C./0.3 mmHg-94% yield.
$[\alpha]_D^{20}$=+110.5° (c=2%, ethanol).
$^1$H-NMR (200 MHz, CDCl$_3$-TMS): delta (ppm): 1.65–1.82 (m, 1H); 2.07–2.55 (m, 3H); 3.77–3.88 (m, 1H); 4.42 (AXq, 2H, delta$_A$=4.91, delta$_X$=3.94, J$_{AX}$=14.8 Hz); 5.06–5.21 (m, 2H); 5.50–5.70 (m, 1H); 7.37–7.55 (m, 4H).

(5S)-1-(3-bromo-5-isoxazolylmethyl)-5-ethenyl-2-pyrrolidinone b.p.=120°–125° C./0.25 mmHg-66% yield.
$[\alpha]_D^{20}$=+56.0° (c=2%, ethanol).
$^1$H-NMR (200 MHz, CDCl$_3$-TMS): delta (ppm): 1.70–1.90 (m, 1H); 2.17–2.48 (m, 3H); 3.97–4.06 (s, 1H); 4.48 (ABq, 2H, delta$_A$=4.82, delta$_B$=4.14, J$_{AB}$=16 Hz); 5.23–5.33 (m, 2H); 5.54–5.71 (m, 1H); 6.25 (s, 1H).

(5S)-5-ethenyl-1-(2-thienylmethyl)-2-pyrrolidinone b.p.=116° C./0.6 mmHg-86% yield.
$[\alpha]_D^{20}$=+153.1° (c=2%; ethanol).
$^1$H-NMR (200 MHz, CDCl$_3$-TMS): delta (ppm): 1.63–1.80 (m, 1H); 2.07–2.52 (m, 3H); 3.90–3.98 (m, 1H); 4.05 (d, 1H, J=15.2 Hz); 5.04 (d, 1H, J=15.2 Hz); 5.55–5.73 (m, 1H); 6.87–7.26 (m, 3H).

EXAMPLE 2

Preparation of the Racemic Mixture of 1-[(2-chlorophenyl)methyl]-5-ethenyl-2-pyrrolidinone A solution of 2-chlorobenzylamine (15.8 g; 0.05 moles) in absolute ethanol (23.4 ml) was added rapidly to 6,6-dimethyl-2-ethenyl-5,7-dioxaspiro[2,5]octane-4,8-dione (9.81 g; 0.05 moles), cooled in ice-bath and under stirring.

During the addition the temperature arose up to about 35° C. and then it came back rapidly to the room value.

The reaction mixture was kept overnight at rest and then it was heated under reflux for 1.5 hours.

After evaporation of the solvent, the residue was dissolved in ethyl ether (240 ml), washed with 10% HCl and then extracted with a NaHCO$_3$ solution. The aqueous phase was washed with ethyl ether, acidified with 10% HCl and extracted with ethyl ether.

The collected organic extracts were washed with water and dried on sodium sulfate.

After evaporation of the solvent, the obtained residue was heated at 185°–195° C. for 15 minutes.

By distillation at 125°–130° C./0.3 mmHg 1-[(2-chlorophenyl)methyl]-5-ethenyl-2-pyrrolidinone (8.8 g; 75% yield) was obtained as racemic mixture.

$^1$H-NMR (200 MHz, CDCl$_3$-TMS): delta (ppm): 1.71–1.87 (m, 1H); 2.13–2.61 (m, 3H); 3.92 (m, 1H); 4.54 (AMq, 2H, delta$_A$=4.88, delta$_M$=4.20, J$_{AM}$=15.6 Hz); 5.06–5.19 (m, 2H); 5.55–5.73 (m, 1H); 7.15–7.35 (m, 4H).

EXAMPLE 3

Preparation of
(5S)-1-(diphenylmethyl)-5-ethenyl-2-pyrrolidinone

A solution of (5S)-5-ethenyl-2-pyrrolidinone (2.2 g; 0.02 moles), diphenylmethanol (7.37 g; 0.04 moles) and p.toluensulfonic acid monohydrate (7.61 g; 0.04 moles) in acetic acid (25 ml) was heated under reflux for 1.5 hours.

After cooling, the solution was poured into water (100 ml) and extracted with ethyl ether.

The organic phase was washed with a saturated NaHCO$_3$ aqueous solution, with water, dried on Na$_2$SO$_4$ and evaporated to dryness. The residue was purified by chromatography on silica gel, using as eluents, first hexane: ethyl acetate=95:5 in order to remove p.toluenesulfonic acid diphenylmethyl ester and then ethyl acetate. An oil was obtained and purified by distillation at 170° C./0.4 mmHg (2 g; 36% yield)

m.p.=64°–65° C. (isopropyl ether).
$[\alpha]_D^{20}$=+15.1° (c=2%, ethanol).
$^1$H-NMR (200 MHz, CDCl$_3$-TMS): delta (ppm): 1.73–1.90 (m, 1H); 2.17–2.64 (m, 3H); 3.97–4.07 (m, 1H); 4.77–4.86 (m, 2H); 5.50–5.68 (m, 1H); 6.26 (s, 1H); 7.18–7.36 (m, 10H).

EXAMPLE 4

Preparation of Diastereoisomers (5S,2'S) and (5S,2'R) of
1-[(2-chlorophenyl)methyl]-5-oxiranyl-2-pyrrolidinone A mixture of (5S)-1-[(2-chlorophenyl)methyl]-5-ethenyl-2-pyrrolidinone (29.2 g; 0.1239 moles), prepared as described in example 1, and of 85% 3-chloroperbenzoic acid (55.6 g; 0.2740 moles) in chloroform (302 ml) was kept at 40° C. for 24 hours.

After cooling, the organic phase was extracted with 10% NaOH (5×30 ml), washed with water and dried on sodium sulfate. After evaporation of the solvent, the residue was purified by chromatography (Jobin Yvon Chromatospac, silica gel, eluent ethyl acetate: petroleum ether=8:2) obtaining the two diastereoisomers (5S,2'S) and (5S,2'R) of 1-[(2-chlorophenyl)methyl]-5-oxiranyl-2-pyrrolidinone (20.2 g; 65% yield) in a ratio (5S,2'S):(5S,2'R)=67:33.

Diastereoisomer (5S,2'S).
m.p.=81°–83° C. (cyclohexane: n.hexane=1:1).
$[\alpha]_D^{20}$=+43.3° (c=2%, ethanol).
$^1$H-NMR (200 MHz, CDCl$_3$-TMS): delta (ppm): 1.91–2.27 (m, 2H); 2.35–2.73 (m, 4H); 2.22–2.88 (m, 1H); 3.23–3.32 (m, 1H); 4.68 (ABq, 2H, delta$_A$=4.88, delta$_B$=4.48, J$_{AB}$=15.8 Hz); 7.16–7.38 (m, 4H).

Diastereoisomer (5S,2'R).
m.p.=75°–76° C. (cyclohexane: n.hexane=1:1).
$[\alpha]_D^{20}$=+80.2° (c=2%, ethanol).
$^1$H-NMR (200 MHz, CDCl$_3$-TMS): delta (ppm): 1.85–2.02 (m, 1H); 2.11–2.30 (m, 1H); 2.39–2.76 (m, 4H); 2.89–2.96 (m, 1H); 3.11–3.22 (m, 1H); 4.78 (ABq, 2H, delta$_A$=5.00, delta$_B$=4.55, J$_{AB}$=15.8 Hz); 7.15–7.41 (m, 4H).

By working in a similar way the following couples of diastereoisomers were prepared.

(5R,2'R) and
(5R,2'S)-1-[(2-chlorophenyl)methyl]-5-oxiranyl-2-pyrrolidinone ratio (5R,2'R):(5R,2'S)=71:29-72% yield.
Diastereoisomer (5R,2'R).
m.p.=75°–76° C. (isopropyl ether).
$[\alpha]_D^{20}$=−43.0° (c=2%, ethanol).
$^1$H-NMR (200 MHz, CDCl$_3$-TMS): delta (ppm): 1.91–2.27 (m, 2H); 2.35–2.73 (m, 4H); 2.22–2.88 (m, 1H); 3.23–3.32 (m, 1H); 4.68 (ABq, 2H, delta$_A$=4.88, delta$_B$=4.48, J$_{AB}$=15.8 Hz); 7.16–7.38 (m, 4H).

Diastereoisomer (5R,2'S).

m.p.=84°-85° C. (isopropyl ether).
$[\alpha]_D^{20}=-78.2°$ (c=2%, ethanol).
¹H-NMR (200 MHz, CDCl₃-TMS): delta (ppm): 1.85-2.02 (m, 1H); 2.11-2.30 (m, 1H); 2.39-2.76 (m, 4H); 2.89-2.96 (m, 1H); 3.11-3.22 (m, 1H); 4.78 (ABq, 2H, delta_A=5.00, delta_B=4.55, J_AB=15.8 Hz); 7.15-7.41 (m, 4H).

(5S,2'S) and (5S,2'R)-5-oxiranyl-1-(phenylmethyl)-2-pyrrolidinone ratio (5S,2'S):(5S,2'R)=66:34-75% yield.
Diastereoisomer (5S,2'S).
oil; $[\alpha]_D^{20}=+57.7°$ (c=2%, ethanol).
¹H-NMR (200 MHz, CDCl₃-TMS): delta (ppm): 1.87-2.22 (m, 2H); 2.32-2.70 (m, 4H); 2.77-2.84 (m, 1H); 3.17-3.27 (m, 1H); 4.52 (AMq, 2H, delta_A=4.85, delta_M=4.19, J_AM=15.0 Hz); 7.17-7.35 (m, 5H).
Diastereoisomer (5S,2'R).
oil; $[\alpha]_D^{20}=+111.7°$ (c=2%, ethanol).
¹H-NMR (200 MHz, CDCl₃-TMS): delta (ppm): 1.75-1.93 (m, 1H); 1.99-2.19 (m, 1H); 2.31-2.62 and 2.72-2.76 (m, 4H); 2.84-2.91 (m, 1H); 2.99-3.10 (m, 1H); 4.61 (AMq, 2H, delta_A=4.96, delta_M=4.27, J_AM=14.6 Hz); 7.18-7.37 (m, 5H).

(5S,2'S) and (5S,2'R)-1-[(2-fluorophenyl)methyl]-5-oxiranyl-2-pyrrolidinone ratio (5S,2'S):(5S,2'R)=71:29-73% yield.
Diastereoisomer (5S,2'S).
oil; $[\alpha]_D^{20}=+47.5°$ (c=2%, ethanol).
¹H-NMR (200 MHz, CDCl₃-TMS): delta (ppm): 1.86-2.21 (m, 2H); 2.28-2.61 and 2.70-2.74 (m, 4H); 2.79-2.86 (m, 1H); 3.18-3.27 (m, 1H); 4.57 (ABq, 2H, delta_A=4.80, delta_B=4.34, J_AB=15.2 Hz); 6.95-7.11 (m, 2H); 7.17-7.32 (m, 2H).
Diastereoisomer (5S,2'R).
oil; $[\alpha]_D^{20}=+84.0°$ (c=2%, ethanol).
¹H-NMR (200 MHz, CDCl₃-TMS): delta (ppm): 1.78-1.96 (m, 1H); 2.04-2.23 (m, 1H); 2.32-2.62 and 2.69-2.73 (m, 1H); 2.84-2.92 (m, 1H); 3.06-3.17 (m, 1H); 4.68 (ABq, 2H, delta_A=4.93, delta_B=4.43, J_AB=15.2 Hz); 6.97-7.09 (m, 2H); 7.15-7.32 (m, 2H).

(5S,2'S) and (5S,2'R)-1-[(3-methoxyphenyl)methyl]-5-oxiranyl-2-pyrrolidinone ratio (5S,2'S):(5S,2'R)=67:33-30% yield.
Diastereoisomer (5S,2'S).
oil; $[\alpha]_D^{20}=+53.2°$ (c=2%, ethanol).
¹H-NMR (200 MHz, CDCl₃-TMS): delta (ppm): 1.87-2.03 (m, 1H); 2.07-2.22 (m, 1H); 2.32-2.64 and 2.68-2.72 (m, 4H); 2.80-2.86 (m, 1H); 3.20-3.29 (m, 1H); 3.76 (s, 3H); 4.49 (AMq, 2H, delta_A=4.84, delta_M=4.14, J_AM=15.1 Hz); 6.72-6.81 (m, 3H); 7.21 (dd, 1H).
Diastereoisomer (5S,2'R).
oil; $[\alpha]_D^{20}=+117.3°$ (c=2%, ethanol).
¹H-NMR (200 MHz, CDCl₃-TMS): delta (ppm): 1.75-1.93 (m, 1H); 2.01-2.20 (m, 1H); 2.31-2.62 and 2.72-2.77 (m, 4H); 2.85-2.93 (m, 1H); 3.01-3.12 (m, 1H); 3.77 (s, 3H); 4.59 (AMq, 2H, delta_A=4.94, delta_M=4.24, J_AM=14.6 Hz); 6.75-6.94 (m, 3H); 7.21 (dd, 1H).

(5S,2'S) and (5S,2'R)-1-[(3,4-dichlorophenyl)methyl]-5-oxiranyl-2-pyrrolidinone ratio (5S,2'S):(5S,2'R)=59:41-60% yield.
Diastereoisomer (5S,2'S).
oil; $[\alpha]_D^{20}=+26.5°$ (c=2%, ethanol).
¹H-NMR (200 MHz, CDCl₃-TMS): delta (ppm): 1.88-2.07 (m, 1H); 2.11-2.26 (m, 1H); 2.34-2.65 and 2.72-2.76 (m, 4H); 2.82-2.88 (m, 1H); 3.28-3.37 (m, 1H); 4.47 (AMq, 2H, delta_A=4.75, delta_B=4.19, J_AM=15.2 Hz); 7.08 (dd, 1H); 7.32 (d, 1H, J=2 Hz); 7.39 (d, 1H, J=8.4 Hz).
Diastereoisomer (5S,2'R).
oil; $[\alpha]_D^{20}=+86.3°$ (c=2.4%, ethanol).
¹H-NMR (200 MHz, CDCl₃-TMS): delta (ppm): 1.76-1.94 (m, 1H); 2.04-2.22 (m, 1H); 2.31-2.61 and 2.74-2.78 (m, 4H); 2.80-2.87 (m, 1H); 2.94-3.05 (m, 1H); 4.54 (AMq, 2H, delta_A=4.81, delta_M=4.28, J_AM=14.7 Hz); 7.20 (dd, 1H); 7.34 (d, 1H, J=8.4 Hz); 7.44 (d, 1H, J=2 Hz).

(5S,2'S) and (5S,2'R)-1-[(4-bromophenyl)methyl]-5-oxiranyl-2-pyrrolidinone

79% yield.
Diastereoisomer (5S,2'S).
oil; $[\alpha]_D^{20}=+39.9°$ (c=2%, ethanol).
¹H-NMR (200 MHz, CDCl₃-TMS): delta (ppm): 1.84-2.20 (m, 2H); 2.30-2.72 (m, 4H); 2.82 (m, 1H); 3.19-3.28 (m, 1H); 4.44 (ABq, 2H, delta_A=4.74, delta_B=4.15, J_AB=15 Hz); 7.05-7.43 (m, 4H).
Diastereoisomer (5S,2'R).
oil; $[\alpha]_D^{20}=+88.6°$ (c=2%, ethanol).
¹H-NMR (200 MHz, CDCl₃-TMS): delta (ppm): 1.73-1.92 (m, 1H); 2.00-2.18 (m, 1H); 2.29-2.60 (m, 3H); 2.72-2.76 (m, 1H); 2.80-2.87 (m, 1H); 2.93-3.04 (m, 1H); 4.54 (ABq, 2H, delta_A=4.84, delta_B=4.24, J_AB=14.6 Hz); 7.20-7.42 (m, 4H).

(5S,2'S) and (5S,2'R)-5-oxiranyl-1-[(3-trifluoromethylphenyl)methyl]-2-pyrrolidinone ratio (5S,2'S):(5S,2'R)=60:40-93% yield.
Diastereoisomer (5S,2'S).
oil; $[\alpha]_D^{20}=+20.3°$ (c=2%, ethanol).
¹H-NMR (200 MHz, CDCl₃-TMS): delta (ppm): 1.75-1.94 (m, 1H); 2.00-2.20 (m, 1H); 2.31-2.52 (m, 3H); 2.71-2.76 (m, 1H); 2.80-2.86 (m, 1H); 2.93-3.04 (m, 1H); 4.64 (ABq, 2H, delta_A=4.92, delta_B=4.36, J_AB=14.7 Hz); 7.34-7.58 (m, 4H).
Diastereoisomer (5S,2'R).
oil; $[\alpha]_D^{20}=+77.5°$ (c=2%, ethanol).
¹H-NMR (200 MHz, CDCl₃-TMS): delta (ppm): 1.87-2.24 (m, 2H); 2.32-2.54 (m, 3H); 2.64-2.70 (m, 1H); 2.80 (m, 1H); 3.21-3.30 (m, 1H); 4.55 (ABq, 2H, delta_A=4.81, delta_B=4.30, J_AB=15.2 Hz); 7.40-7.53 (m, 4H).

(5S,2'S) and (5S,2'R)-1-(3-bromo-5-isoxazolylmethyl)-5-oxiranyl-2-pyrrolidinone ratio (5S,2'S):(5S,2'R)=46:54-52.3% yield.
Diastereoisomer (5S,2'S).
oil; $[\alpha]_D^{20}=+19.4°$ (c=2%, ethanol).
¹H-NMR (200 MHz, CDCl₃-TMS): delta (ppm): 1.86-2.53 (m, 4H); 2.60-2.86 (m, 2H); 2.90-2.96 (m, 1H); 3.45-3.56 (m, 1H); 4.60 (ABq, 2H, delta_A=4.81, delta_B=4.40, J_AB=16.6 Hz); 6.30 (s, 1H).
Diastereoisomer (5S,2'R).
oil; $[\alpha]_D^{20}=+56.4°$ (c=2.5%, ethanol).
¹H-NMR (200 MHz, CDCl₃-TMS): delta (ppm): 1.80-1.98 (m, 1H); 2.10-2.60 (m, 4H); 2.76-2.80 (m, 1H);

2.85–2.93 (m, 1H); 3.10–3.20 (m, 1H); 4.72 (ABq, 2H, delta$_A$=4.90, delta$_B$=4.54, J$_{AB}$=16 Hz); 6.31 (s, 1H).

(5S,2'S) and (5S,2'R)-1-(diphenylmethyl)-5-oxiranyl-2-pyrrolidinone ratio (5S,2'S):(5S,2'R)=86:14–81% yield.
Diastereoisomer (5S,2'S).
m.p. =87°–88° C. (isopropyl ether).
[α]$_D^{20}$= −97.2° (c=2%, ethanol).
$^1$H-NMR (200 MHz, CDCl$_3$-TMS): delta (ppm): 1.87–1.91 (m, 1H); 2.00–2.22 (m, 2H); 2.24–2.28 (m, 1H); 2.34–2.49 (m, 1H); 2.58–2.76 (m, 2H); 3.30–3.39 (m, 1H); 6.57 (s, 1H); 7.14–7.38 (m, 10H).
Diastereoisomer (5S,2'R).
m.p. =104°–105° C. (isopropyl ether).
[α]$_D^{20}$= +5.2° (c=2%, ethanol).
$^1$H-NMR (200 MHz, CDCl$_3$-TMS): delta (ppm): 1.18–2.23 (m, 2H); 2.30–2.66 (m, 4H); 2.80–2.86 (m, 1H); 3.30–3.41 (m, 1H); 6.37 (s, 1H); 7.25–7.42 (m, 10H).

EXAMPLE 5

Preparation of 1-[(5S)-2-oxo-1-(2-thienylmethyl)-5-pyrrolidinyl]-1,2-ethanediol Diastereoisomeric Mixture A solution of osmium tetroxide (0.032 g; 0.000126 moles) in t.butanol (3 ml) was added to a solution of (5S)-5-ethenyl-1-(2-thienylmethyl)-2-pyrrolidinone (6.22 g; 0.03 moles), prepared as described in example 1, and N-methylmorpholine N-oxide monohydrate (4.46 g; 0.033 moles) in acetone (15 ml) and water (6 ml), at room temperature and under nitrogen.

The reaction mixture was kept under stirring at room temperature for about 16 hours under nitrogen; then it was diluted with water (25 ml), sodium hydrosulfite (0.4 g) and magnesium trisilicate (4.5 g) were added.

After 10 minutes under stirring, the reaction mixture was filtered, washing with acetone:water=1:1.

The filtrate was treated with 1N sulfuric acid up to pH 7 and it was evaporated to dryness under vacuum at 60° C.

The residue was dissolved in water, the solution was acidified up to pH 2 with 1N H$_2$SO$_4$, saturated with sodium chloride and extracted with ethyl acetate (9×40 ml).

The collected organic phases were washed with a sodium chloride saturated solution, dried on Na$_2$SO$_4$ and evaporated to give a mixture of (1S,5'S) and (1R,5'S)-1-[2-oxo-1-(2-thienylmethyl)-5-pyrrolidinyl]-1,2-ethanediol in a ratio (1S,5'S):(1R,5'S)=75:25 in quantitative yield.

$^1$H-NMR (200 MHz, CDCl$_3$-TMS): delta (ppm): 1.68–2.09 (m, 2H, A+B); 2.19–2.58 (m, 2H, A+B); 3.45–3.66 (m, 3H, A+B); 3.71–3.81 (m, 1H, B); 4.03–4.09 (m, 1H, A); 4.26 (d, 1H, J=15.4 Hz, A); 4.80 (ABq, 2H, delta$_A$=5.07, delta$_B$=4.53, J$_{AB}$=15.3 Hz, B); 5.07 (d, 1H, J=15.4 Hz, A); 6.86–7.25 (m, 3H, A+B).

EXAMPLE 6

Preparation of (5S,2'S) and (5S,2'R)-5-oxiranyl-1-(2-thienylmethyl)-2-pyrrolidinone A solution of methanesulfonyl chloride (4.19 g; 0.0366 moles) in dichloromethane (28 ml) was added dropwise to a mixture of 1-[(5S)-2-oxo-1-(2-thienylmethyl)-5-pyrrolidinyl]-1,2-ethanediol (6.68 g; 0.02768 moles), prepared as described in example 5, benzyltriethylammonium chloride (0.28 g; 0.00124 moles), dichloromethane (28 ml) and 20% (w/w) sodium hydroxide solution (33.4 g; 0.167 moles), under reflux and vigorous stirring.

The reaction mixture was, then, kept under stirring at the same temperature for 1.5 hours.

After cooling and dilution with water (55 ml), the organic phase was separated, washed with water up to neutral pH, dried on sodium sulfate and evaporated to give a mixture of (5S,2'S) and (5S,2'R)-5-oxiranyl-1-(2-thienylmethyl)-2-pyrrolidinone (5.8 g; 94% yield) in a ratio (5S,2'S):(5S,2'R)=2:1, as an oil.

The two diastereoisomers were separated by chromatography (Jobin Yvon Chromatospac, silica gel, eluent ethyl acetate:hexane=8:2)

Diastereoisomer (5S,2'S).
oil; [α]$_D^{20}$= +62.5° (c=2%, ethanol).
$^1$H-NMR (200 MHz, CDCl$_3$-TMS): delta (ppm): 1.85–2.60 (m, 5H); 2.78 (m, 1H); 2.89 (m, 1H); 3.32–3.41 (m, 1H); 4.67 (ABq, 2H, delta$_A$=5.01, delta$_B$=4.34, J$_{AB}$=15.5 Hz); 6.89–6.93 (m, 2H); 7.18–7.21 (m, 1H).
Diastereoisomer (5S,2'R).
oil; [α]$_D^{20}$= +106.7° (c=2%, ethanol).
$^1$H-NMR (200 MHz, CDCl$_3$-TMS): delta (ppm): 1.68–1.91 (m, 1H); 2.00–2.18 (m, 1H); 2.26–2.57 (m, 3H); 2.75–2.79 (m, 1H); 2.86–2.94 (m, 1H); 3.04–3.18 (m, 1H); 4.76 (ABq, 2H, delta$_A$=5.05, delta$_B$=4.49, J$_{AB}$=15.2 Hz); 6.87–6.92 (m, 1H); 7.02–7.05 (m, 1H); 7.16–7.19 (m, 1H).

EXAMPLE 7

Preparation of (1S)-1-[(5S)-1-[(2-chlorophenyl)methyl]-2-oxo-5-pyrrolidinyl]-2-[(2R,2'R)-disec.butylamino]ethanol (Compound 1)

A solution of (5S,2'R)-1-[(2-chlorophenyl)methyl]-5-oxiranyl-2-pyrrolidinone (9.5 g; 0.03774 moles), prepared as described in example 4, and (R,R)-disec.butylamine (6.34 g; 0.04906 moles) in n.butanol (19.5 ml) was heated under reflux for 70 hours.

After evaporation of the solvent, the residue was dissolved in cooled 5% HCl (50 ml) and extracted with ethyl ether (2×50 ml). The aqueous phase was basified with K$_2$CO$_3$ and extracted with ethyl ether which was, then, washed with water, dried on sodium sulfate and evaporated.

The residue was purified by chromatography (silica gel, eluent CHCl$_3$:1N methanolic ammonia=98:2) obtaining Compound 1 (7.2 g; 50% yield).
m.p. =71°–73° C. (n.hexane).
[α]$_D^{20}$= −64.6° (c=1%, methanol).
$^1$H-NMR (200 MHz, CDCl$_3$-TMS): delta (ppm): 0.84 (t, 6H); 0.90 (d, 6H); 1.12–1.46 (m, 4H); 1.80–2.59 (m, 8H); 3.54–3.67 (m, 2H); 3.93 (bs, 1H); 4.78 (AMq, 2H, delta$_A$=4.97, delta$_M$=4.43, J$_{AM}$=15.7 Hz); 7.13–7.36 (m, 4H).

The absolute configuration was verified by X-ray analysis.

By working in a similar way the following compounds were prepared.

(1R)-1-[(5S)-1-[(2-chlorophenyl)methyl]-2-oxo-5-pyrrolidinyl]-2-[(2R,2'R)-disec.butylamino]ethanol (Compound 2)

m.p. =96°–98° C. (n.hexane)-73% yield.
[α]$_D^{20}$= +20.0° (c=1%, methanol).
$^1$H-NMR (200 MHz, CDCl$_3$-TMS): delta (ppm): 0.81 (t, 6H); 0.95 (d, 6H); 1.15 (m, 2H); 1.40 (m, 2H);

1.80–2.68 (m, 8H); 3.44 (ddd, 1H); 3.52 (bs, 1H); 3.75 (ddd, 1H); 4.70 (AMq, 2H, delta$_A$=4.97, delta$_M$=4.43, J$_{AM}$=15.7 Hz); 7.13–7.35 (m, 4H).

(1S)-1-[(5R)-1-[(2-chlorophenyl)methyl]-2-oxo-5-pyrrolidinyl]-2-[(2R,2'R)-disec.butylamino]ethanol (Compound 3)

m.p.=58°–60° C. (n.hexane)-66% yield.
[α]$_D^{20}$=−47.9° (c=1%, methanol).
$^1$H-NMR (200 MHz, CDCl$_3$-TMS): delta (ppm): 0.86 (t, 6H); 0.93 (d, 6H); 1.15–1.50 (m, 4H); 1.83–2.70 (m, 8H); 3.39 (ddd, 1H); 3.69 (bs, 1H); 3.83 (ddd, 1H); 4.71 (AMq, 2H, delta$_A$=4.98, delta$_M$=4.44, J$_{AM}$=15.8 Hz); 7.14–7.36 (m, 4H).

(1R)-1-[(5R)-1-[(2-chlorophenyl)methyl]-2-oxo-5-pyrrolidinyl]-2-[(2R,2'R)-disec.butylamino]ethanol (Compound 4)

m.p.=59°–61° C. (n.hexane)-40% yield.
[α]$_D^{20}$=−27.8° (c=1%, methanol).
$^1$H-NMR (200 MHz, CDCl$_3$-TMS): delta (ppm): 0.85 (t, 6H); 0.98 (d, 6H); 1.18 (m, 2H); 1.51 (m, 2H); 1.77–2.78 (m, 8H); 3.49–3.64 (m, 2H); 3.50–4.00 (bs, 1H); 4.81 (ABq, 2H, delta$_A$=5.00, delta$_B$=4.61, J$_{AB}$=15.7 Hz); 7.14–7.37 (m, 4H).

(1R)-1-[(5S)-1-[(2-chlorophenyl)methyl]-2-oxo-5-pyrrolidinyl]-2-[(2S,2'S)-disec.butylamino]ethanol (Compound 5)

m.p.=58°–60° C. (n.hexane)-70% yield.
[α]$_D^{20}$=+49.0° (c=1%, methanol). $^1$H-NMR (200 MHz, CDCl$_3$-TMS): delta (ppm): 0.86 (t, 6H); 0.93 (d, 6H); 1.16–1.50 (m, 4H); 1.83–2.70 (m, 8H); 3.39 (ddd, 1H); 3.70 (bs, 1H); 3.82 (ddd, 1H); 4.71 (AMq, 2H, delta$_A$=4.97, delta$_M$=4.45, J$_{AM}$=15.8 Hz); 7.14–7.37 (m, 4H).

(1S)-1-[(5S)-1-[(2-chlorophenyl)methyl]-2-oxo-5-pyrrolidinyl]-2-[(2S,2'S)-disec.butylamino]ethanol (Compound 6)

m.p.=64°–65° C. (n.hexane)-56% yield.
[α]$_D^{20}$=+24.8° (c=1%, methanol).
$^1$H-NMR (200 MHz, CDCl$_3$-TMS): delta (ppm): 0.85 (t, 6H); 0.97 (d, 6H); 1.06–1.30 (m, 2H); 1.39–1.60 (m, 2H); 1.76–1.91 (m, 4H); 1.96–2.20 (m, 2H); 2.32–2.77 (m, 5H); 3.47–3.61 (m, 2H); 4.13 (bs, 1H); 4.81 (ABq, 2H, delta$_A$=5.00, delta$_B$=4.62, J$_{AB}$=15.7 Hz); 7.13–7.37 (m, 4H).

(1R)-1-[(5S)-1-[(2-chlorophenyl)methyl]-2-oxo-5-pyrrolidinyl]-2-[(2R,2'S)-disec.butylamino]ethanol (Compound 7)

m.p.=68°–70° C. (n.hexane)-70% yield.
[α]$_D^{20}$=+16.5° (c=1%, methanol).
$^1$H-NMR (200 MHz, CDCl$_3$-TMS): delta (ppm): 0.79 (t, 3H); 0.82 (t, 3H); 0.88 (d, 3H); 0.96 (d, 3H); 1.00–1.57 (m, 4H); 1.78–2.10 (m, 2H); 2.14–2.66 (m, 6H); 3.37 (ddd, 1H); 3.68 (bs, 1H); 3.86 (ddd, 1H); 4.67 (AMq, 2H, delta$_A$=4.95, delta$_M$=4.39, J$_{AM}$=15.8 Hz); 7.10–7.32 (m, 4H).

(1S)-1-[(5S)-1-[(2-chlorophenyl)methyl]-2-oxo-5-pyrrolidinyl]-2-[(2R,2'S)-disec.butylamino]ethanol (Compound 8)

oil-80% yield.
[α]$_D^{20}$=−27.1° (c=1%, methanol).
$^1$H-NMR (200 MHz, CDCl$_3$-TMS): delta (ppm): 0.80 (t, 3H); 0.81 (t, 3H); 0.88 (d, 3H); 0.95 (d, 3H); 0.91–1.59 (m, 4H); 1.74–2.16 (m, 3H); 2.28–2.60 (m, 5H); 3.47–3.61 (m, 2H); 3.99 (bs, 1H); 4.76 (ABq, 2H, delta$_A$=4.93, delta$_B$=4.59, J$_{AB}$=15.7 Hz); 7.09–7.34 (m, 4H).

(1S)-1-[(5R)-1-[(2-chlorophenyl)methyl]-2-oxo-5-pyrrolidinyl]-2-[(2S,2'S)-disec.butylamino]ethanol (Compound 9)

m.p.=96°–99° C. (n.hexane)-68% yield.
[α]$_D^{20}$=+18.4° (c=1%, methanol).
$^1$H-NMR (200 MHz, CDCl$_3$-TMS): delta (ppm): 0.74 (t, 6H); 0.91 (d, 6H, J=6.5 Hz); 1.00–1.45 (m, 4H); 1.77–2.11 (m, 2H); 2.19–2.65 (m, 6H); 3.42–3.50 (m, 1H); 3.72–3.80 (m, 1H); 4.66 (ABq, 2H, delta$_A$=4.94, delta$_B$=4.38, J$_{AB}$=16 Hz); 7.11–7.31 (m, 4H).

(1S)-1-[(5R)-1-[(2-chlorophenyl)methyl]-2-oxo-5-pyrrolidinyl]-2-[(2R,2'S)-disec.butylamino]ethanol (Compound 10)

m.p.=66°–67° C. (n.hexane)-68% yield.
[α]$_D^{20}$=−15.0° (c=1%, methanol).
$^1$H-NMR (200 MHz, CDCl$_3$-TMS): delta (ppm): 0.78 (t, 3H); 0.81 (t, 3H); 0.87 (d, 3H, J=6.6 Hz); 0.95 (d, 3H, J=6.6 Hz); 1.00–1.56 (m, 4H); 1.77–2.1 (m, 2H); 2.14–2.65 (m, 6H); 3.33–3.40 (m, 1H); 3.73–3.81 (m, 1H); 4.66 (ABq, 2H, delta$_A$=4.94, delta$_B$=4.38, J$_{AB}$=16 Hz); 7.10–7.31 (m, 4H).

(1R)-1-[(5R)-1-[(2-chlorophenyl)methyl]-2-oxo-5-pyrrolidinyl]-2-[(2S,2'S)-disec.butylamino]ethanol (Compound 11)

m.p.=72°–73° C. (n.hexane)-45% yield.
[α]$_D^{20}$=+65.8° (c=1%, methanol).
$^1$H-NMR (200 MHz, CDCl$_3$-TMS): delta (ppm): 0.862 (d, 6H, J=6.5 Hz); 0.985 (t, 6H); 1.09–1.40 (m, 4H); 1.76–1.91 (m, 1H); 1.96–2.15 (m, 2H); 2.30–2.54 (m, 5H); 3.50–3.62 (m, 2H); 3.88 (bs, 1H); 4.75 (ABq, 2H, delta$_A$=4.89, delta$_B$=4.61, J$_{AB}$=15.5 Hz); 7.10–7.32 (m, 4H).

(1R)-1-[(5R)-1-[(2-chlorophenyl)methyl]-2-oxo-5-pyrrolidinyl]-2-[(2R,2'S)-disec.butylamino]ethanol (Compound 12)

oil; 70% yield.
[α]$_D^{20}$=+25.8° (c=1%, methanol).
$^1$H-NMR (200 MHz, CDCl$_3$-TMS): delta (ppm): 0.82 (t, 3H); 0.83 (t, 3H); 0.89 (d, 3H, J=6.5 Hz); 0.973 (d, 3H, J=7 Hz); 1.01–1.58 (m, 4H); 1.76–1.91 (m, 1H); 1.95–2.18 (m, 2H); 2.31–2.61 (m, 5H); 3.43–3.64 (m, 2H); 4.01 (bs, 1H); 4.77 (ABq, 2H, delta$_A$=4.95, delta$_B$=4.60, J$_{AB}$=15.7 Hz); 7.13–7.36 (m, 4H).

(1R)-1-[(5S)-2-oxo-1-(phenylmethyl)-5-pyrrolidinyl]-2-[(2R,2'R)-disec.butylamino]ethanol (Compound 13)

m.p.=103°–104° C. (isopropyl ether)-73% yield.
[α]$_D^{20}$=−15.3° (c=1%, methanol).
$^1$H-NMR (200 MHz, CDCl$_3$-TMS): delta (ppm): 0.80 (t, 6H); 0.94 (d, 6H); 1.03–1.49 (m, 4H); 1.79–2.09 (m, 2H); 2.18–2.41 (m, 2H); 2.45–2.63 (m, 4H); 3.50 (ddd, 1H); 3.55 (bs, 1H); 3.72 (ddd, 1H); 4.56 (AXq, 2H, delta$_A$=4.99, delta$_X$=4.12, J$_{AX}$=15.0 Hz); 7.17–7.34 (m, 5H).

(1S)-1-[(5S)-2-oxo-1-(phenylmethyl)-5-pyrrolidinyl]-2-[(2R,2'R)-disec.butylamino]ethanol (Compound 14)

m.p.=53°–55° C. (n.hexane)-51% yield.
[α]$_D^{20}$=−57.6° (c=2%, ethanol).
$^1$H-NMR (200 MHz, CDCl$_3$-TMS): delta (ppm): 0.84 (t, 6H); 0.88 (d, 6H); 1.13–1.46 (m, 4H); 1.69–2.16 (m, 4H); 2.25–2.54 (m, 4H); 3.49–3.62 (m, 2H); 4.07 (bs, 1H); 4.66 (ABq, 2H, delta$_A$=4.82, delta$_B$=4.50, J$_{AB}$=14.5 Hz); 7.16–7.34 (m, 5H).

(1R)-1-[(5S)-1-[(2-fluorophenyl)methyl]-2-oxo-5-pyrrolidinyl]-2-[(2R,2'R)-disec.butylamino]ethanol (Compound 15)

m.p.=115°–116° C. (isopropyl ether)-72% yield.
[α]$_D^{20}$=−20.8° (c=1%, methanol).
$^1$H-NMR (200 MHz, CDCl$_3$-TMS): delta (ppm): 0.82 (t, 6H); 0.96 (d, 6H); 1.05–1.29 (m, 2H); 1.33–1.53 (m, 2H); 1.76–2.10 (m, 2H); 2.18–2.39 (m, 2H); 2.46–2.66 (m, 4H); 3.44 (ddd, 1H); 3.51 (bs, 1H); 3.78 (ddd, 1H); 4.61 (AMq, 2H, delta$_A$=4.92, delta$_M$=4.31, J$_{AM}$=15.1 Hz); 6.95–7.35 (m, 4H).

(1S)-1-[(5S)-1-[(2-fluorophenyl)methyl]-2-oxo-5-pyrrolidinyl]-2-[(2R,2'R)-disec.butylamino]ethanol (Compound 16)

m.p.=50°–52° C. (n.hexane)-40% yield.
[α]$_D^{20}$=−53.9° (c=2%, ethanol).
$^1$H-NMR (200 MHz, CDCl$_3$-TMS): delta (ppm): 0.84 (t, 6H); 0.88 (d, 6H); 1.12–1.46 (m, 4H); 1.74–2.57 (m, 8H); 3.53–3.66 (m, 2H); 3.98 (bs, 1H); 4.71 (ABq, 2H, delta$_A$=4.87, delta$_B$=4.55, J$_{AB}$=15.2 Hz); 6.94–7.01 (m, 2H); 7.15–7.33 (m, 2H).

(1R)-1-[(5S)-1-[(3-methoxyphenyl)methyl]-2-oxo-5-pyrrolidinyl]-2-[(2R,2'R)-disec.butylamino]ethanol (Compound 17)

m.p.=74°–76° C. (n.hexane)-60% yield.
[α]$_D^{20}$=−9.3° (c=1%, methanol).
$^1$H-NMR (200 MHz, CDCl$_3$-TMS): delta (ppm): 0.79 (t, 6H); 0.93 (d, 6H); 1.03–1.24 (m, 2H); 1.29–1.49 (m, 2H); 1.75–2.06 (m, 2H); 2.19–2.41 (m, 2H); 2.45–2.62 (m, 4H); 3.47–3.55 (m, 1H); 3.60 (bs, 1H); 3.74 (s, 3H); 3.69–3.77 (m, 1H); 4.52 (AMq, 2H, delta$_A$=4.96, delta$_M$=4.09, J$_{AM}$=15.2 Hz); 6.73–6.82 (m, 3H); 7.15–7.24 (m, 1H).

(1S)-1-[(5S)-1-[(3-methoxyphenyl)methyl]-2-oxo-5-pyrrolidinyl]-2-[(2R,2'R)-disec.butylamino]ethanol (Compound 18)

oil; 70% yield.
[α]$_D^{20}$=−51.1° (c=1%, methanol).
$^1$H-NMR (200 MHz, CDCl$_3$-TMS): delta (ppm): 0.83 (t, 6H); 0.86 (d, 6H); 1.11–1.44 (m, 4H); 1.67–2.15 (m, 3H); 2.23–2.53 (m, 5H); 3.48–3.60 (m, 2H); 3.73 (s, 3H); 4.07 (bs, 1H); 4.62 (ABq, 2H, delta$_A$=4.78, delta$_B$=4.46, J$_{AB}$=14.6 Hz); 6.71–6.77 (m, 1H); 6.85–6.90 (m, 1H); 7.13–7.24 (m, 1H).

(1R)-1-[(5S)-1-[(3,4-dichlorophenyl)methyl]-2-oxo-5-pyrrolidinyl]-2-[(2R,2'R)-disec.butylamino]ethanol (Compound 19)

m.p.=116°–117° C. (isopropyl ether)-69% yield.
[α]$_D^{20}$=−10.0° (c=2%, methanol).
$^1$H-NMR (200 MHz, CDCl$_3$-TMS): delta (ppm): 0.84 (t, 6H); 0.97 (d, 6H); 1.06–1.30 (m, 2H); 1.34–1.54 (m, 2H); 1.82–2.05 (m, 2H); 2.19–2.65 (m, 2H); 3.51–3.59 (m, 1H); 3.61–3.70 (m, 1H); 3.30–3.80 (bs, 1H); 4.54 (AMq, 2H, delta$_A$=4.87, delta$_M$=4.20, J$_{AM}$=15.2 Hz); 7.13 (dd, 1H); 7.36 (d, 1H, J=2.2 Hz); 7.38 (d, 1H, J=8.4 Hz).

(1S)-1-[(5S)-1-[(3,4-dichlorophenyl)methyl]-2-oxo-5-pyrrolidinyl]-2-[(2R,2'R)-disec.butylamino]ethanol (Compound 20)

oil; 59% yield.
[α]$_D^{20}$=−48.9° (c=2%, ethanol).
$^1$H-NMR (200 MHz, CDCl$_3$-TMS): delta (ppm): 0.82 (t, 6H); 0.87 (d, 6H); 1.10–1.44 (m, 4H); 1.56–1.73 (m, 1H); 1.85–2.11 (m, 2H); 2.20–2.55 (m, 5H); 3.33–3.49 (m, 2H); 4.23 (bs, 1H); 4.63 (ABq, 2H, delta$_A$=4.71, delta$_B$=4.55, J$_{AB}$=14.6 Hz); 7.18 (dd, 1H); 7.30 (d, 1H, J=8.2 Hz); 7.43 (d, 1H, J=2 Hz).

(1R)-1-[(5S)-1-(3-bromo-5-isoxazolylmethyl)-2-oxo-5-pyrrolidinyl]-2-[(2R,2'R)-disec.butylamino]ethanol (Compound 21)

m.p.=111°–112.5° C. (isopropyl ether)-55% yield.
[α]$_D^{20}$=−42.2° (c=1%, methanol).
$^1$H-NMR (200 MHz, CDCl$_3$-TMS): delta (ppm): 0.85 (t, 6H); 0.98 (d, 6H); 1.08–1.30 (m, 2H); 1.39–1.60 (m, 2H); 1.91–2.03 (m, 2H); 2.20–2.71 (m, 6H); 3.63–3.77 (m, 3H); 4.66 (ABq, 2H, delta$_A$=4.90, delta$_B$=4.43, J$_{AB}$=16.1 Hz); 6.33 (s, 1H).

(1S)-1-[(5S)-1-(3-bromo-5-isoxazolylmethyl)-2-oxo-5-pyrrolidinyl]-2-[(2R,2'R)-disec.butylamino]ethanol (Compound 22)

oil; 58% yield.
[α]$_D^{20}$=−46.1° (c=1%, methanol).
$^1$H-NMR (200 MHz, CDCl$_3$-TMS): delta (ppm): 0.86 (t, 3H); 0.94 (d, 6H); 1.16–1.45 (m, 4H); 1.95–2.65 (m, 8H); 3.41–3.54 (m, 2H); 4.89 (ABq, 2H, delta$_A$=4.95, delta$_B$=4.84, J$_{AB}$=16 Hz); 6.27 (s, 1H).

(1R)-1-[(5S)-2-oxo-1-[(3-trifluoromethylphenyl)methyl]-5-pyrrolidinyl]-2-[(2R,2'R)-disec.butylamino]ethanol (Compound 23)

m.p.=86.5°–87.5° C. (isopropyl ether)-77% yield.
[α]$_D^{20}$=−26.4° (c=1%, methanol).
$^1$H-NMR (200 MHz, CDCl$_3$-TMS): delta (ppm): 0.754 (t, 6H); 0.91 (d, 6H, J=6.5 Hz); 1.00–1.46 (m, 4H); 1.78–2.07 (m, 2H); 2.20–2.63 (m, 6H); 3.47–3.55 (m, 1H); 3.64–3.75 (bs, 2H); 4.61 (AXq, 2H, delta$_A$=4.98, delta$_X$=4.24, J$_{AX}$=15.7 Hz); 7.35–7.50 (m, 4H).

(1S)-1-[(5S)-2-oxo-1-[(3-trifluoromethylphenyl)methyl]-5-pyrrolidinyl]-2-[(2R,2'R)-disec.butylamino]ethanol (Compound 24)

oil; 54% yield.
[α]$_D^{20}$=−50.6° (c=1%, methanol).
$^1$H-NMR (200 MHz, CDCl$_3$-TMS): delta (ppm): 0.80–0.90 (m, 12H); 1.13–1.46 (m, 4H); 1.60–1.72 (m, 1H); 1.87–2.11 (m, 2H); 2.27–2.57 (m, 5H); 3.35–3.53 (m, 2H); 4.27 (s, 1H); 4.76 (ABq, 2H, delta$_A$=4.88, delta$_B$=4.64, J$_{AB}$=14.5 Hz); 7.34–7.61 (m, 4H).

(1R)-1-[(5S)-1-[(4-bromophenyl)methyl]-2-oxo-5-pyrrolidinyl]-2-[(2R,2'R)-disec.butylamino]ethanol (Compound 25)

oil; 81% yield.
[α]$_D^{20}$=−10.2° (c=1%, methanol).
$^1$H-NMR (200 MHz, CDCl$_3$-TMS): delta (ppm): 0.83 (t, 6H); 0.88 (d, 6H, J=5.7 Hz); 1.14–1.41 (m, 4H); 1.63–1.80 (m, 1H); 1.85–2.13 (m, 2H); 2.22–2.50 (m, 5H); 3.42–3.53 (m, 2H); 4.06–4.21 (bs, 1H); 4.62 (ABq, 2H, delta$_A$=4.72, delta$_B$=4.53, J$_{AB}$=14.5 Hz); 7.18–7.40 (m, 4H).

(1S)-1-[(5S)-1-[(4-bromophenyl)methyl]-2-oxo-5-pyrrolidinyl]-2-[(2R,2'R)-disec.butylamino]ethanol (Compound 26)

m.p. = 132°–133° C. (isopropyl ether)-55% yield.
$[\alpha]_D^{20} = -53.6°$ (c=1%, methanol).
$^1$H-NMR (200 MHz, CDCl$_3$-TMS): delta (ppm): 0.80 (t, 6H); 0.94 (d, 6H, J=6.5 Hz); 1.04–1.49 (m, 4H); 1.77–2.04 (m, 2H); 2.18–2.61 (m, 6H); 3.46–3.53 (m, 1H); 3.55–3.73 (bs, 1H); 4.50 (ABq, 2H, delta$_A$=4.88, delta$_B$=4.12, J$_{AB}$=15 Hz); 7.09–7.42 (m, 4H).

(1R)-1-[(5S)-1-(diphenylmethyl)-2-oxo-5-pyrrolidinyl]-2-[(2R,2'R)-disec.butylamino]ethanol (Compound 27)

amorphous solid-71% yield.
$[\alpha]_D^{20} = -75.4°$ (c=1%, methanol).
$^1$H-NMR (200 MHz, CDCl$_3$-TMS): delta (ppm): 0.77 (t, 6H); 0.85 (d, 6H); 0.92–1.42 (m, 4H); 1.83–2.51 (m, 7H); 2.70–2.90 (m, 1H); 3.21–3.31 (m, 2H); 6.50 (s, 1H); 7.12–7.38 (m, 10H).

(1S)-1-[(5S)-1-(diphenylmethyl)-2-oxo-5-pyrrolidinyl]-2-[(2R,2'R)-disec.butylamino]ethanol (Compound 28)

m.p. = 84°–85° C. (isopropyl ether)-39.4% yield.
$^1$H-NMR (200 MHz, CDCl$_3$-TMS): delta (ppm): 0.76 (t, 6H); 0.80 (d, 6H, J=6.5 Hz); 1.07–1.32 (m, 4H); 2.02–2.31 (m, 6H); 2.40–2.50 (m, 2H); 3.00–3.08 (m, 1H); 3.65 (bs, 1H); 4.05–4.12 (m, 1H); 6.40 (s, 1H); 7.20–7.34 (m, 10H).

(1R)-1-[(5S)-2-oxo-1-(2-thienylmethyl)-5-pyrrolidinyl]-2-[(2R,2'R)-disec.butylamino]ethanol (Compound 29)

m.p. = 78°–79° C. (n.hexane)-74.3% yield.
$[\alpha]_D^{20} = -19.2°$ (c=1%, methanol).
$^1$H-NMR (300 MHz, CDCl$_3$-TMS): delta (ppm): 0.88 (t, 6H); 1.00 (d, 6H, J=6.7 Hz); 1.15–1.30 (m, 2H); 1.43–1.56 (m, 2H); 1.85–2.03 (m, 2H); 2.24–2.38 (m, 2H); 2.46–2.67 (m, 4H); 3.64 (m, 1H); 3.79 (m, 1H); 4.75 (ABq, 2H, delta$_A$=5.14, delta$_B$=4.37, J$_{AB}$=15.38 Hz); 6.92–7.22 (2m, 3H).

(1S)-1-[(5S)-2-oxo-1-(2-thienylmethyl)-5-pyrrolidinyl]-2-[(2R,2'R)-disec.butylamino]ethanol (Compound 30)

m.p. = 65.5°–67° C. (isopropyl ether)-73.5% yield.
$[\alpha]_D^{20} = -48.6°$ (c=1%, methanol).
$^1$H-NMR (300 MHz, CDCl$_3$-TMS): delta (ppm): 0.90 (t, 6H); 0.94 (d, 6H, J=6.5 Hz); 1.23–1.48 (m, 4H); 1.72 (m, 1H); 1.98 (m, 1H); 2.14 (m, 1H); 2.26–2.61 (m, 5H); 3.60 (m, 2H); 4.89 (ABq, 2H, delta$_A$=5.03, delta$_B$=4.76, J$_{AB}$=15.0 Hz); 6.91–7.20 (3m, 3H).

EXAMPLE 8

Preparation of
(1R)-1-[(5S)-1-[(2-chlorophenyl)methyl]-2-oxo-5-pyrrolidinyl]-2-piperidinoethanol (Compound 31)

A solution of (5S,2'S)-1-[(2-chlorophenyl)methyl]-5-oxiranyl-2-pyrrolidinone (4 g; 0.016 moles), prepared as described in example 4, and piperidine (2.72 g; 0.032 moles) in ethanol (8.3 ml) was heated under reflux for 20 hours.

After evaporation of the solvent, the residue was dissolved in 5% HCl and extracted with ethyl ether.

The aqueous phase was basified with K$_2$CO$_3$ and extracted with ethyl ether which was, then, washed with water, dried on sodium sulfate and evaporated.

A thick oil (4.84 g) was obtained and crystallized from n.hexane (75 ml) to give Compound 31 (3.45 g; 64% yield) as a white crystalline solid.
m.p. = 65°–67° C.
$[\alpha]_D^{20} = +43.7°$ (c=1%, methanol).
$^1$H-NMR (200 MHz, CDCl$_3$-TMS): delta (ppm) 1.31–1.57 (m, 6H); 1.76–2.64 (m, 10H); 3.27 (ddd, 1H); 3.62 (bs, 1H); 3.96 (ddd, 1H); 4.66 (AMq, 2H, delta$_A$=4.97, delta$_M$=4.35, J$_{AM}$=15.8 Hz); 7.11–7.34 (m, 4H).

By working in a similar way the following compounds were prepared.

(1S)-1-[(5S)-1-[(2-chlorophenyl)methyl]-2-oxo-5-pyrrolidinyl]-2-piperidinoethanol (Compound 32)

oil; 88% yield.
$[\alpha]_D^{20} = -7.3°$ (c=1%, methanol).
$^1$H-NMR (200 MHz, CDCl$_3$-TMS): delta (ppm): 1.31–1.57 (m, 6H); 1.71–2.31 (m, 6H); 2.36–2.55 (m, 4H); 3.47–3.57 (m, 1H); 3.66–3.76 (m, 1H); 3.88 (bs, 1H); 4.77 (ABq, 2H, delta$_A$=4.94, delta$_B$=4.60, J$_{AB}$=15.8 Hz); 7.10–7.35 (m, 4H).

(1R)-1-[(5S)-1-[(2-chlorophenyl)methyl]-2-oxo-5-pyrrolidinyl]-2-diisopropylaminoethanol (Compound 33)

m.p. = 113.5°–114.5° C. (isopropyl ether)-72% yield.
$[\alpha]_D^{20} = +29.2°$ (c=1%, methanol).
$^1$H-NMR (200 MHz, CDCl$_3$-TMS): delta (ppm): 0.918 (d, 6H, J=6.6 Hz); 0.981 (d, 6H, J=6.6 Hz); 1.80–2.66 (m, 6H); 2.96 (m, 2H); 3.34–3.41 (m, 1H); 3.73–3.81 (m, 2H); 4.67 (ABq, 2H, delta$_A$=4.97, delta$_B$=4.38, J$_{AB}$=15.4 Hz); 7.11–7.33 (m, 4H).

(1S)-1-[(5S)-1-[(2-chlorophenyl)methyl]-2-oxo-5-pyrrolidinyl]-2-diisopropylaminoethanol (Compound 34)

m.p. = 73°–75° C. (isopropyl ether)-54.6% yield.
$[\alpha]_D^{20} = -21.1°$ (c=1%, methanol).
$^1$H-NMR (200 MHz, CDCl$_3$-TMS): delta (ppm): 0.91 (d, 6H, J=6.5 Hz); 0.96 (d, 6H, J=6.5 Hz); 1.73–1.89 (m, 1H); 1.94–2.17 (m, 2H); 2.29–2.57 (m, 3H); 2.91 (m, 2H); 3.46–3.61 (m, 2H); 4.78 (ABq, 2H, delta$_A$=4.96, delta$_B$=4.61, J$_{AB}$=15.6 Hz); 7.10–7.33 (m, 4H).

(1R)-1-[(5S)-1-[(2-chlorophenyl)methyl]-2-oxo-5-pyrrolidinyl]-2-dicyclopentylaminoethanol (Compound 35)

m.p. = 79°–80° C. (isopropyl ether)-60% yield.
$[\alpha]_D^{20} = +29.7°$ (c=1%, methanol).
$^1$H-NMR (200 MHz, CDCl$_3$-TMS): delta (ppm): 1.14–1.77 (m, 16H); 1.83–2.13 (m, 2H); 2.25–2.41 (m, 3H); 2.49–2.66 (m, 1H); 3.03–3.20 (m, 2H); 3.32–3.40 (m, 1H); 3.71–3.90 (m, 2H); 4.68 (AMq, 2H, delta$_A$=4.96, delta$_M$=4.39, J$_{AM}$=16 Hz); 7.12–7.34 (m, 4H).

(1S)-1-[(5S)-1-[(2-chlorophenyl)methyl]-2-oxo-5-pyrrolidinyl]-2-dicyclopentylaminoethanol (Compound 36)

oil; 68% yield.
$[\alpha]_D^{20} = -29.4°$ (c=1%, methanol).
$^1$H-NMR (200 MHz, CDCl$_3$-TMS): delta (ppm): 1.13–1.88 (m, 17H); 1.93–2.24 (m, 2H); 2.29–2.56 (m, 3H); 3.02–3.18 (m, 2H); 3.39–3.61 (m, 2H); 3.63–4.54 (bs, 1H); 4.78 (AMq, 2H, delta$_A$=4.97, delta$_M$=4.60, J$_{AM}$=15.5 Hz); 7.10–7.35 (m, 4H).

(1R)-1-[(5S)-1-[(2-chlorophenyl)methyl]-2-oxo-5-pyrrolidinyl]-2-[[(R)-sec.butyl]isopropylamino]ethanol (Compound 37)

m.p. = 116°–117° C. - 74.5% yield.
$[\alpha]_D^{20} = +3.5°$ (c=5%, methanol).

¹H-NMR (200 MHz, CDCl₃-TMS): delta (ppm): 0.80 (t, 3H); 0.92 (d, 3H, J=6.6 Hz); 0.96 (d, 3H, J=6.6 Hz); 0.97 (d, 3H, J=6.6 Hz); 1.02–1.53 (m, 2H); 1.80–2.12 (m, 2H); 2.17–2.67 (m, 5H); 2.94 (m, 1H); 3.44–3.66 (m, 1H); 3.67 (bs, 1H); 3.72–3.80 (m, 1H); 4.68 (ABq, 2H, delta$_A$=4.97, delta$_B$=4.40, J$_{AB}$=16 Hz); 7.13–7.34 (m, 4H).

(1S)-1-[(5S)-1-[(2-chlorophenyl)methyl]-2-oxo-5-pyrrolidinyl]-2-[[(R)-sec.butyl]isopropylamino]ethanol (Compound 38)

m.p.=44°–46° C. - 58.4% yield.
[α]$_D^{20}$=−47.7° (c=1%, methanol).
¹H-NMR (200 MHz, CDCl₃-TMS): delta (ppm): 0.83 (t, 3H); 0.89 (d, 3H, J=6.6 Hz); 0.91 (d, 3H, J=6.6 Hz); 0.974 (d, 3H, J=6.6 Hz); 1.11–1.44 (m, 2H); 1.76–1.95 (m, 1H); 1.96–2.19 (m, 2H); 2.30–2.62 (m, 4H); 2.89 (m, 1H); 3.50–3.65 (m, 2H); 4.77 (ABq, 2H, delta$_A$=4.94, delta$_B$=4.61, J$_{AB}$=15.8 Hz); 7.11–7.34 (m, 4H).

(1S)-1-[(5S)-1-[(2-chlorophenyl)methyl]-2-oxo-5-pyrrolidinyl]-2-(dicyclobutylamino)ethanol (Compound 39)

oil; 82% yield.
[α]$_D^{20}$=−17.68° (c=1%, methanol).
¹H-NMR (200 MHz, CDCl₃-TMS): delta (ppm): 1.44–1.66 (m, 4H); 1.65–2.07 (m, 10H); 2.16–2.21 (m, 2H); 2.38–2.47 (m, 2H); 3.04 (m, 2H); 3.46–3.63 (m, 2H); 4.75 (ABq, 2H, delta$_A$=4.97, delta$_B$=4.57, J$_{AB}$=15.2 Hz); 7.13–7.35 (m, 4H).

(1S)-1-[(5S)-1-[(2-chlorophenyl)methyl]-2-oxo-5-pyrrolidinyl]-2-[bis(1-ethylpropyl)amino]ethanol (Compound 40)

m.p.=73°–75° C. (n. hexane)-25% yield.
[α]$_D^{20}$=−37.2° (c=1%, methanol).
¹H-NMR (200 MHz, CDCl₃-TMS): delta (ppm): 0.84 (t, 6H); 0.88 (t, 6H); 1.00–1.62 (m, 8H); 1.77–2.23 (m, 5H); 2.30–2.61 (m, 3H); 3.50–3.66 (m, 2H); 4.75 (ABq, 2H, delta$_A$=4.96, delta$_B$=4.54, J$_{AB}$=15.5 Hz); 7.12–7.36 (m, 4H).

EXAMPLE 9

Preparation of the racemic mixture of 1-[(2-chlorophenyl)methyl]-6-ethenyl-2-piperidinone By working in a way similar to that described in example 1 and starting from 6-ethenyl-2-piperidinone (m.p.=53°–56.5° C. from n.hexane), prepared according to the method described in European patent application No. 144664, 1-[(2-chlorophenyl)methyl]-6-ethenyl-2-piperidinone was obtained with 73% yield.
M.p.=37°–39° C. (n.hexane)-b.p.=132°–134° C./0.2 mmHg.
¹H-NMR (200 MHz, CDCl₃-TMS): delta (ppm): 1.67–1.93 (m, 4H); 2.34–2.56 (m, 2H); 3.85 (m, 1H); 4.07 (d, 1H, J=16 Hz); 5.27 (d, 1H, J=16 Hz); 5.06–5.24 (m, 2H); 5.71 (m, 1H); 7.01–7.32 (m, 4H).

EXAMPLE 10

Preparation of the two racemic mixtures of 1-[(2-chlorophenyl)methyl]-6-oxiranyl-2-piperidinone By working in a way similar to that described in example 4 and starting from the racemic mixture of 1-[(2-chlorophenyl)methyl]-6-ethenyl-2-piperidinone, prepared as described in example 9, 1-[(2-chlorophenyl)methyl]-6-oxiranyl-2-piperidinone was obtained as a mixture of the two racemic mixtures in a ratio 2.5:1 which were separated by chromatography on silica gel (eluent ethyl acetate:n.hexane=7:3).

Racemic mixture A (higher Rf).
oil; 45.2% yield.
¹H-NMR (200 MHz, CDCl₃-TMS): delta (ppm): 1.76–2.10 (m, 4H); 2.50–2.59 (m, 2H); 2.72–2.76 (m, 1H); 2.85–2.92 (m, 1H); 2.98–3.06 (m, 1H); 4.81 (ABq, 2H, delta$_A$=5.11, delta$_B$=4.51, J$_{AB}$=16.2 Hz); 7.11–7.35 (m, 4H).

Racemic mixture B (lower Rf).
m.p.=96°–98° C. (ethyl acetate) - 17.8% yield.
¹H-NMR (200 MHz, CDCl₃-TMS): delta (ppm): 1.78–2.05 (m, 4H); 2.38–2.41 (m, 1H); 2.50–2.57 (m, 2H); 2.68–2.73 (m, 1H); 2.97–3.02 (m, 2H); 4.90 (ABq, 2H, delta$_A$=5.22, delta$_B$=4.58, J$_{AB}$=16.6 Hz); 7.10–7.35 (m, 4H).

EXAMPLE 11

Preparation of 1-[2-[(2-chlorophenyl)methyl]-2-oxo-6-piperidinyl]-2-[(2R,2'R)-disec.butylamino]ethanol (Compounds 41, 42 and 43)

By working in a way similar to that described in example 7 and starting from the racemic mixtures A and B of 1-[(2-chlorophenyl)methyl]-6-oxiranyl-2-piperidinone, prepared as described in example 10, the two diastereoisomeric couples C and D of 1-[-[(2-chlorophenyl)methyl]-2-oxo-6-piperidinyl]-2-[(2R,2'R)-disec.butylamino]ethanol were obtained respectively.

Each diastereoisomer of couple C (RSRR) and (SRRR) was separated by chromatography on silica gel (eluent toluene:diethylamine=98:2) obtaining the pure diastereoisomers compound 41 and compound 42.

Less polar diastereoisomer (Compound 41).
oil; [α]$_D^{20}$=−24.7° (c=1%, methanol).
¹H-NMR (200 MHz, CDCl₃-TMS): delta (ppm): 0.84 (t, 6H); 0.94 (d, 6H, J=6.6 Hz); 1.20–1.43 (m, 4H); 1.63–1.80 (m, 2H); 1.95–2.13 (m, 2H); 2.25–2.65 (m, 6H); 3.16–3.24 (m, 1H); 3.71–3.81 (m, 1H); 4.42 (d, 1H, J=15.8 Hz); 5.25 (d, 1H, J=15.8 Hz); 7.11–7.34 (m, 4H).

More polar diastereoisomer (Compound 42).
m.p.=113°–114° C. (n.hexane).
[α]$_D^{20}$=−41.5° (c=1%, methanol).
¹H-NMR (200 MHz, CDCl₃-TMS): delta (ppm): 0.80 (t, 6H); 0.95 (d, 6H, J=6.7 Hz); 1.02–1.24 (m, 2H); 1.32–1.53 (m, 2H); 1.62–1.79 (m, 2H); 1.90–2.12 (m, 2H); 2.23–2.35 (m, 1H); 2.45–2.70 (m, 5H); 3.21–3.28 (m, 1H); 3.64–3.73 (m, 2H); 4.46 (d, 1H, J=16 Hz); 5.18 (d, 1H, J=16 Hz); 7.10–7.33 (m, 4H).

Diastereoisomeric couple D (Compound 43).
ratio RRRR:SSRR=1:1.
m.p.=100°–103° C. (n.hexane) - 60.5% yield.
[α]$_D^{20}$=−34.3° (c=1%, methanol).
¹H-NMR (200 MHz, CDCl₃-TMS): delta (ppm): 0.848 (t, 6H); 0.858 (t, 6H); 0.92 (d, 6H, J=6.5 Hz); 0.98 (d, 6H, J=6.5 Hz); 1.06–1.57 (m, 8H); 1.74–1.83 (m, 8H); 2.04–2.18 (m, 2H); 2.46–2.65 (m, 9H); 2.71–2.80 (m, 1H); 3.17–3.31 (m, 2H); 3.61–3.80 (m, 2H); 4.58–4.68 (m, 2H); 5.33–5.46 (m, 2H); 7.10–7.34 (m, 8H).

EXAMPLE 12

The compounds object of the present invention underwent the following in vitro pharmacological tests.
(1) Evaluation of the competition for binding of [³H]-dihydromorphine (DHM) to opioid receptors in rat-brain homogenate The experiments were carried out according to the method described by Simon et al. [Proc. Nat. Acad. Sci. U.S.A., 70, pp. 1947–1949, (1973)].

Sprague-Dawley rats weighing about 150 g were used.

The animals were decapitated and, after removal of cerebellum, the brains were homogenized in 50 nM Tris-HCl buffer (pH 7.4) containing 0.32M saccharose. The homogenate was centrifugated at 1000 rpm for 10 minutes and the supranatant was centrifugated again at 20000 rpm for 20 minutes.

The obtained pellet was suspended in a homogenization buffer without saccharose up to a protein concentration of 2 mg/ml. The incubating system consisted in: 500 µl of homogenate (1 mg of proteins), 390 µl of 50 mM Tris-HCl buffer (pH 7.4), 100 µl of a solution at different concentrations of the compounds of formula I or of 10 µM Naloxone for the determination of the aspecific binding and 10 µl of $^3$H-DHM (specific activity 87.7 Ci/moles, 1 nM final concentration). The mixture was incubated at 25° C. for 30 minutes after the addition of the radioactive binder.

Then, the samples were filtered through Whatman GF/B filters, washed twice with 3 ml volumes of buffer and dried in oven at 70° C. Filters were put in scintillation vials with 15 ml of Filter Count (Packard) scintillation cocktail and the radioactivity was evaluated by a Packard Tricarb 4530 scintillation counter with 60% efficiency.

The activity was expressed as inhibiting concentration ($IC_{50}$) 50% of the binding of $^3$H-DHM.

In table 1 the $IC_{50}$ values obtained for some representative compounds of formula I are reported.

TABLE 1

Competition ($IC_{50}$) of Compound 1, Compound 14, Compound 16, Compound 22 and Compound 26 for specific binding of $^3$H-DHM to rat-brain homogenate in comparison with morphine.

| Compound | $IC_{50}$ (nM) |
| --- | --- |
| 1 | 0.9 |
| 14 | 3.3 |
| 16 | 2.5 |
| 22 | 9.4 |
| 36 | 10.0 |
| morphine | 1.5 |

(2) Evaluation of the morphine-like activity on guinea-pig isolated ileum

The experiments were carried out according to the method described by Goldstein and Schultz (Br. J. Pharmacol., 48, 655, 1975) which is based on the capacity of the molecules showing an agonist activity on opioid receptors to inhibit the contractions of smooth muscles of guinea-pig ileum induced by electric stimulation (0.1 Hz–0.5 msec.).

The pharmacological activity was expressed as the necessary concentration (mM) to inhibit 50% of contraction ($IC_{50}$).

In table 2 the $IC_{50}$ values obtained for some representative compounds of formula I are reported.

TABLE 2

Morphine-like activity on guinea-pig isolated ileum of some compounds of formula I expressed as $IC_{50}$ (nM) in comparison with morphine.

| Compound | $IC_{50}$ (nM) |
| --- | --- |
| 1 | 0.03 |
| 3 | 4.6 |
| 4 | 8.7 |
| 5 | 50.0 |

TABLE 2-continued

Morphine-like activity on guinea-pig isolated ileum of some compounds of formula I expressed as $IC_{50}$ (nM) in comparison with morphine.

| Compound | $IC_{50}$ (nM) |
| --- | --- |
| 7 | 70.0 |
| 8 | 44.0 |
| 12 | 83.0 |
| 14 | 0.43 |
| 15 | 40.0 |
| 16 | 0.29 |
| 18 | 0.28 |
| 19 | 0.77 |
| 20 | 0.23 |
| 22 | 4.96 |
| 24 | 2.9 |
| 26 | 0.04 |
| 34 | 44.71 |
| 36 | 4.06 |
| 38 | 21.54 |
| 40 | 60.0 |
| 43 | 0.5 |
| morphine | 111.0 |

EXAMPLE 13

The compounds object of the present invention were tested in vivo in order to evaluate the central analgesic activity.

The hot plate test was carried out on mouse according to the method described by Eddy et al. (J. Pharmacol., 98, 121, 1950). The compounds were administered by systemic route (oral and subcutaneous). The analgesic activity was expressed as 50% effective dose ($ED_{50}$).

In table 3 the results obtained for some representative compounds of formula I are reported.

TABLE 3

Analgesic activity ($ED_{50}$) of some compounds of formula I in comparison with morphine.

| Compound | $ED_{50}$ (C.L. 95%) | |
| --- | --- | --- |
| | mg/kg/s.c. | mg/kg/os |
| 1 | 0.011 | 2.6 |
| 4 | 3.8 | — |
| 8 | 1.4 | — |
| 14 | 0.04 | 6.5 |
| 16 | 0.03 | 5.8 |
| 18 | 0.07 | — |
| 20 | 0.28 | — |
| 22 | 1.00 | — |
| 24 | 0.5 | — |
| 26 | 0.03 | — |
| 36 | 4.7 | — |
| 38 | 1.1 | — |
| 43 | 0.1 | — |
| morphine | 3.5 | 18.0 |

EXAMPLE 14

The compounds object of the present invention were tested in vivo in order to evaluate the capacity to induce physical dependence. The Jumping test described by Sealens et al. [Committee on Problems of Drug Dependence, vol. 2, (1971), page 1310] was used. In a period of 2 days, 7 intraperitoneal administrations at geometrically increasing doses of the compounds of formula I and of morphine were carried out starting from a dose corresponding to the $ED_{50}$ value obtained in mouse after subcutaneous administration.

After 4 hours from the last administration, the animals were treated with Naloxone (10 mg/kg i.p.) and the number of jumps taken by the animals during the period of 15 minutes after the administration of Naloxone was counted.

For the compounds which did not show abstinence syndrome the experiments were repeated by carrying out a double number of treatments (total 14).

In table 4, for exemplifying purposes, the percentage of jumping animals obtained for a compound of formula I is reported.

TABLE 4

Jumping test on mouse: a comparison between Compound 1 and morphine.

| Compound | Total dose (mg/kg i.p.) | Percentage of jumping animals |
|---|---|---|
| 1 | 3.8 | 5% |
| morphine | 156.0 | 80% |

The compound of formula I in jumping test showed a significant decrease in the percentage of jumping mice in comparison with morphine. Similar results were obtained with the other compounds of formula I.

Therefore, the compounds object of the present invention, contrary to morphine, do not induce physical dependence.

EXAMPLE 15

For exemplifying purposes the following pharmaceutical preparations containing a compound of formula I as active ingredient are reported.

Capsules for oral use:

| Compound 1 | 200 g |
|---|---|
| Talc | 30 g |
| Magnesium stearate | 20 g |
| Lactose | 750 g |

The ingredients were put in a mixer and mixed for 15 minutes. The so obtained mixture was granulated and distributed into about 4000 hard gelatine capsules each containing 50 mg of active ingredient.

Vials for injectable use:

| Compound 1 as hydrochloric salt | 10 g |
|---|---|
| Physiologic solution | 20 l |

The solution of the active ingredient in physiologic solution was filtered through 0.22 μm membrane filter and distributed into vials, dosing 1 ml each vial. The vials were closed and sterilized in autoclave at 121° C. for 25 minutes.

About 20,000 vials each containing 0.5 mg of active ingredient were obtained.

In a similar way pharmaceutical compositions containing the other compounds of formula I and their pharmaceutically useful salts were prepared.

What we claim is:

1. A compound of the formula (I)

$$O= \underset{\underset{\underset{R}{|}}{\underset{CH-R_3}{|}}}{\overset{(CH_2)_n}{\underset{N}{\diagup}}} \diagdown \underset{CH-CH_2-N}{\overset{OH}{|}} \diagdown \underset{R_2}{\overset{R_1}{\diagup}}$$

wherein
R is phenyl optionally substituted by 1 to 3 substituents selected from the group consisting of $C_1-C_4$ alkyl, $C_1-C_4$ alkoxy, hydroxy, halogen and trifluoromethyl;
$R_1$ and $R_2$, the same or different, are linear or branched $C_1-C_6$ alkyl or $C_3-C_6$ cycloalkyl;
$R_3$ is hydrogen or phenyl optionally substituted by 1 to 3 substituents selected from the group consisting of $C_1-C_4$ alkyl, $C_1-C_4$ alkoxy, hydroxy, halogen and trifluoromethyl; and
n is 1;
or a salt thereof with a pharmaceutically acceptable acid.

2. A compound according to claim 1 wherein R is phenyl optionally substituted by 1 to 3 substituents selected from the group consisting of chlorine, bromine, methyl, ethyl, methoxy, ethoxy, hydroxy and trifluoromethyl and $R_3$ is hydrogen.

3. A compound according to claim 1 wherein $R_1$ and $R_2$ are both sec.butyl.

4. A compound according to claim 1 wherein $R_1$ and $R_2$ are both (R)-sec.butyl.

5. A single stereoisomer of a compound according to claim 1.

6. A pharmaceutical composition with analgesic activity containing an analgesically effective amount of a compound according to claim 1 and a carrier.

7. A method for the treatment of dolorous syndromes consisting in administering an analgesically effective amount of a compound according to claim 1.

8. A method for inducing anaesthesia consisting in administering an anaesthesically effective amount of a compound according to claim 1.

* * * * *